United States Patent [19]

Schnabel et al.

[11] Patent Number: 4,504,676

[45] Date of Patent: Mar. 12, 1985

[54] PREPARATION OF DIACYLOXYBUTENES

[75] Inventors: Rolf Schnabel, Schifferstadt; Gerd Kissau, Muenster; Hans-Martin Weitz, Bad Durkheim; Rolf Fischer, Heidelberg, all of Fed. Rep. of Germany

[73] Assignee: BASF Aktiengesellschaft, Ludwigshafen, Fed. Rep. of Germany

[21] Appl. No.: 588,120

[22] Filed: Mar. 9, 1984

[30] Foreign Application Priority Data

Mar. 15, 1983 [DE] Fed. Rep. of Germany ....... 3309168

[51] Int. Cl.$^3$ ........................................... C07C 67/055
[52] U.S. Cl. .................................................... 560/244
[58] Field of Search ........................................ 560/244

[56] References Cited

U.S. PATENT DOCUMENTS

| | | |
|---|---|---|
| 949,739 | 2/1910 | Bataille . |
| 3,755,423 | 8/1973 | Onoda et al. . |
| 4,113,970 | 9/1978 | Tanabe et al. . |
| 4,122,285 | 10/1978 | Weitz et al. . |

FOREIGN PATENT DOCUMENTS

| | | |
|---|---|---|
| 27979 | 6/1982 | European Pat. Off. . |
| 2716000 | 10/1977 | Fed. Rep. of Germany . |
| 2943407 | 5/1981 | Fed. Rep. of Germany . |
| 30616 | 3/1972 | Japan . |
| 72090 | 4/1973 | Japan . |
| 126611 | 2/1975 | Japan . |
| 140406 | 4/1975 | Japan . |
| 1494430 | 12/1977 | United Kingdom . |

Primary Examiner—Michael L. Shippen
Attorney, Agent, or Firm—John H. Shurtleff

[57] ABSTRACT 1,4-diacyloxybutenes are prepared by reacting a 1,3-butadiene with a carboxylic acid and oxygen in the presence of a catalyst in a reactor, by a process in which the 3,4-diacyloxybutene formed as a by-product in the reaction is separated off from the reaction mixture, and some or all of this 3,4-diacyloxybutene is recycled to the reactor.

9 Claims, No Drawings

PREPARATION OF DIACYLOXYBUTENES

The present invention relates to a novel process for the preparation of 1,4-diacyloxybutenes by reacting a 1,3-butadiene with a carboxylic acid and oxygen over a catalyst.

German Pat. No. 2,217,452 discloses that 1,4-diacyloxybutenes (referred to as 1,4-DABE below) are obtained if a 1,3-butadiene is reacted with oxygen and a carboxylic acid over a solid catalyst which contains Pd and one or more of the elements Sb, Bi, Te and Se. German Laid-Open Application DOS No. 2,417,658 discloses that this synthesis from butadiene, oxygen and acetic acid in the gas or liquid phase can also be carried out over a catalyst which contains Pt and one or more elements of main groups 5 and 6. German Laid-Open Application DOS No. 2,542,925 proposes reacting the starting materials in a reactor and avoiding a gas phase. Finally, German Laid-Open Application DOS No. 2,747,634 discloses that, instead of butadiene, a butadiene-containing C4 cracked cut can be used.

In order to be able to utilize these processes industrially, a number of preconditions have to be met. For example, the productivity of the catalyst, i.e. the amount of 1,4-DABE produced per unit time and unit amount of catalyst or noble metal, must not fall below a certain value, since otherwise the cost of the relatively expensive catalyst is not recovered. Moreover, this value must be maintained over a sufficiently long period in order to avoid the time-consuming and expensive procedures of changing or regenerating the catalyst. Since, in addition to 1,4-DABE, the undesirable 3,4-DABE is always formed, it is also very important that the selectivity of the synthesis, i.e. the proportion of 1,4-DABE in the product from the process, does not fall below a certain value.

Since the proportion of 3,4-DABE in the reaction product is substantial, being more than 15% by weight in, for example, the processes described in Japanese Preliminary Published Application Nos. 72,090/1973 and 140,406/1975, it is necessary to convert the 3,4-DABE to 1,4-DABE by isomerization in order to improve the yield of the latter compound. An appropriate isomerization process is described in, for example, Japanese Preliminary Published Application Nos. 30,616/1972 and 126,611/1975. The isomerization inevitably results in a larger number of process stages. Other disadvantages arise from the fact that the isomerization of 3,4-DABE is a relatively inefficient reaction, since 3,4-DABE, being a vinyl compound, tends to undergo undesirable reactions.

Attempts have also been made to develop catalysts having a high selectivity with respect to the formation of 1,4-DABE. For example, German Pat. No. 2,716,000 describes a process in which a catalyst containing Pd and I is used. However, catalysts of this type do not have a long life and therefore have to be changed frequently. Furthermore, there is a high corrosion risk when iodine-containing catalyst systems are used.

We have found that, in the preparation of 1,4-diacyloxybutenes by reacting a 1,3-butadiene with a carboxylic acid and oxygen in the presence of a catalyst in a reactor, the formation of 3,4-DABE can advantageously be suppressed if the 3,4-diacyloxybutene formed as a by-product in the reaction is separated off from the reaction mixture, and some or all of this 3,4-diacyloxybutene is recycled to the reactor.

Suitable dienes, in addition to 1,3-butadiene itself, are substituted butadienes, e.g. isoprene and 2,3-dimethyl-1,3-butadiene, 1,3-pentadienes, e.g. piperylene, and acyloxy-substituted 1,3-butadienes, e.g. 1-acetoxybutadiene, 1-acetoxy-2-methyl-1,3-butadiene and 1-acetoxy-3-methyl-1,3-butadiene. The stated butadienes can be used alone or in a mixture which also contains, for example, other hydrocarbons, such as monoolefins or paraffin hydrocarbons. Such mixtures are available in the form of, for example, C4 cuts.

Particularly suitable carboxylic acids are low molecular weight ones, for example fatty acids of 1 to 3 carbon atoms, such as formic acid, acetic acid or propionic acid.

The catalysts used preferably contain Pd and/or Pt and are advantageously in the form of supported catalysts in which the active components are applied onto the carrier material, e.g. active carbon, $SiO_2$ or $Al_2O_3$. In addition to containing Pd or Pt, the active catalytic material can also contain other metals, such as Te, Cu, Sb, Se or Bi. Catalysts of this type are described in, for example, German Pat. No. 2,217,452, German Laid-Open Applications DOS No. 2,417,658 and DOS No. 2,943,407 and European Pat. No. 27,979.

The reaction for the preparation of the 1,4-acyloxybutenes is carried out in a conventional manner in the gas or liquid phase, for example at from 80 to 120° C. and under from 1 to 100 bar. The reactants are employed in, for example, the following proportions: from 0.2 to 10, preferably from 1 to 5, moles of 1,3-butadiene, from 10 to 100, preferably from 20 to 50, moles of carboxylic acid and from 0.1 to 5, preferably from 0.5 to 2.5, moles of oxygen.

In the novel process, 3,4-DABE is separated off, advantageously by distillation, from the reaction mixture obtained in the catalytic reaction of the 1,3-butadiene with the carboxylic acid and oxygen, and some or all of this 3,4-DABE is recycled to the reactor.

Surprisingly, as a result of recycling 3,4-DABE to the reaction, in accordance with the invention, the formation of further 3,4-DABE is suppressed. This result was not to be expected since the conditions prevailing do not permit isomerization of 3,4-DABE to 1,4-DABE or vice versa, which would lead to the establishment of thermodynamic equilibrium between the isomers (3,4-DABE:1,4-DABE=1:3). This is evident from the fact that, when an additional amount of 3,4-DABE over and above the thermodynamic equilibrium is fed into the reactor, conversion of 3,4-DABE to 1,4-DABE does not take place, and furthermore from the fact that when recycling is discontinued the 3,4-DABE:1,4-DABE ratio, which is apparently under kinetic control, is 1:10 and hence well below the thermodynamic equilibrium ratio. Furthermore, it is surprising that for maximum recycling of 3,4-DABE, when the formation of further 3,4-DABE is virtually completely suppressed, the synthesis of 1,4-DABE can be continued with just as high a space-time yield, without any adverse effect on the catalyst life or the selectivity (no increase in the concentration of byproducts).

The specific procedure is as follows: the reaction of the starting materials in the reactor is carried out in a conventional manner by flooding or trickling, the reactor used being, for example, a fixed-bed reactor or a suspension reactor. If necessary, the oxygen is diluted with inert gases, but it can also be dissolved in the carboxylic acid, in an upstream saturator, and these two reactants can then be passed together into the reactor.

In addition, the 3,4-DABE separated off (advantageously by distillation) from the liquid reaction mixture is fed into the reactor. When the total amount of 3,4-DABE separated off from the reaction mixture is recycled, the formation of further 3,4-DABE is virtually completely suppressed, i.e. the amount of 3,4-DABE recycled is virtually the same as the amount of 3,4-DABE emerging. In this procedure, the 3,4-DABE concentration necessary for complete suppression of the formation of further 3,4-DABE is established automatically after the reaction begins. It then remains constant at about 30% of the value for 1,4-DABE.

Depending on the expected demand for 3,4-DABE, it is also possible to recycle to the reactor only some of the 3,4-DABE separated off from the liquid reaction mixture.

Working up of the reaction mixture may be illustrated using the reaction of 1,3-butadiene with acetic acid and oxygen as an example, the procedure being as follows: the reaction mixture also contains gaseous or dissolved oxygen and may contain inert gases, and these gases can be recovered and reused if, after emerging from the reactor, the reaction mixture is let down to atmospheric or slightly superatmospheric pressure at from 20° to 40° C. As a result, the dissolved oxygen and any inert gases present substantially pass into the gas phase, together with smaller amounts of butadiene and any other hydrocarbons present. The butadiene can be removed from the gas phase by a conventional method, such as washing, for example with acetic acid, or by cooling. Oxygen and any inert gases present can then be recycled to the reactor by means of a compressor.

The liquid reaction mixture, which still contains 1,3-butadiene and may contain other hydrocarbons, is then heated at the boil under atmospheric or slightly superatmospheric pressure, so that butadiene and any other hydrocarbons pass over into the gas phase, while acetic acid and the other higher-boiling components of the reacted mixture remain in the liquid phase. This separation of substances is advantageously carried out in a distillation column. The gaseous butadiene and any other hydrocarbons present are liquefied by a conventional method, for example by cooling and/or compression, and are recycled to the reactor, while unreacted acetic acid is separated off from the diacetoxybutenes in the reaction mixture by distillation under atmospheric pressure, and can likewise be reused.

The high-boiling fraction, which consists of 1,4-diacetoxybutene (1,4-DAcBE) and 3,4-diacetoxybutene (3,4-DAcBE), is then fractionally distilled in order to separate off the 3,4-DAcBE. This is advantageously carried out under reduced pressure, so that the bottom and top temperatures in the column are reduced to such an extent that thermal decomposition or transformation reactions do not take place. Advantageous bottom temperatures are from 150° to 180° C., which requires a pressure of from 60 to 80 mbar. Some or all of the 3,4-DAcBE isolated via the top is recycled to the reactor, in accordance with the invention.

The novel process gives high space-time yields and particularly high selectivities, and these can be maintained over long periods.

The diacyloxybutenes obtainable by the process of the invention are useful intermediates, for example for the preparation of butene-1,4-diol, tetrahydrofuran and butane-1,4-diol. The 1,1,4-triacetoxy-2-methylbut-2-enes or 2-methyl-1,4-diacetoxybut-2-enes obtained in the novel acetoxylation of isoprene or 1-acetoxy-2-methyl-1,3-butadiene are useful intermediates, for example for the synthesis of terpene compounds.

EXAMPLE (a) Conventional procedure 1.25 liters/hour of acetic acid in which 1.3 moles of oxygen have been dissolved, and 0.6 liter/hour of a liquid mixture of 1 part by weight of 1,3-butadiene and 3 parts by weight of butene, are passed into a reaction tube having a capacity of 0.6 liter.

The reaction tube is filled with a solid supported catalyst in which the carrier material is silica gel and the active components are Pd (3.4% by weight), Te (0.8% by weight) and Cu (10.5% by weight). The catalyst has a particle size of 1-3 mm.

The reaction tube is maintained under 70 bar and at 95° C., and, in order to avoid hot spots, the liquid reaction mixture is circulated at a rate of 200 liters hour by means of a pump. During this circulation, the oxygen fed in is dissolved in the liquid phase, in a saturator which forms an integral part of the cycle, so that there is no gas phase in the actual reaction space.

The reaction mixture is removed from this liquid cycle at the rate at which starting materials are fed in, and the mixture removed is then let down to atmospheric pressure. The liquid phase obtained contains, in addition to the principal component acetic acid, 2.1% by weight of 3,4-diacetoxybut-1-ene (3,4-DAcBE), 2.2% by weight of cis-1,4-diacetoxybut-2-ene (cis-1,4-DAcBE) and 18.4% by weight of trans-1,4-diacetoxybut-2-ene (trans-1,4-DAcBE). Acetic acid is distilled off from the mixture at from 120° to 140° C. and under from 1 bar to 130 mbar, after which 3,4-DAcBE is separated off from its mixture with 1,4-DAcBE by distillation in a rectification column having 40 trays, at a bottom temperature of 178° C. and a top temperature of 133° C. and under 80 mbar. 1,4-DAcBE is finally distilled off at 128° C. under 13 mbar. The distillation residue is 0.2% by weight, based on the liquid phase after letting down the pressure and degassing.

(b) Procedure according to the invention 132.5 g/hour of 3,4-DAcBE obtained by separation of the mixture of 1,4-DAcBE and 3,4-DAcBE by distillation are additionally fed into the reaction tube under the conditions stated in section (a). The reaction mixture obtained is let down as described above. The resulting liquid phase contains, in addition to acetic acid, 10.6% by weight of 3,4-DAcBE, 2.2% by weight of cis-1,4-DAcBE and 18.5% by weight of trans-1,4-DAcBE. The amount of 3,4-DAcBE emerging is virtually identical to that fed in. The distillation residue is about 0.2% by weight, as in the procedure described under (a). The activity of the catalyst is unchanged after a test period of 500 hours.

We claim:

1. In a process for the preparation of a 1,4-diacyloxybutene by reacting a 1,3-butadiene with a carboxylic acid and oxygen in the presence of a catalyst containing palladium or platinum in a reactor at a temperature of 80°-120° C. and under a pressure of 1-100 bar, the improvement which comprises:
   fractionally distilling the reaction mixture to separate off the 3,4-diacyloxybutene which is formed as a by-product in the reaction; and
   recycling to the reactor some or all of this 3,4-diacyloxybutene by-product.

2. A process as claimed in claim 1, wherein substantially all of the 3,4-diacyloxybutene separated from the reaction mixture is recycled to the reactor.

3. A process as claimed in claim 1, wherein the carboxylic acid is a fatty acid of 1 to 3 carbon atoms.

4. A process as claimed in claim 1, wherein the carboxylic acid is acetic acid.

5. A process as claimed in claim 1, wherein the catalyst consists essentially of a metal selected from the group consisting of palladium and platinum supported on a carrier selected from the group consisting of active carbon, $SiO_2$ or $Al_2O_3$.

6. A process as claimed in claim 1, wherein the active catalytic material contains an additional metal selected from the group consisting of Te, Cu, Sb, Se or Bi.

7. A process as claimed in claim 1, wherein the active catalyst consists essentially of Pd, Te and Cu supported on a silica gel carrier.

8. A process as claimed in claim 1, wherein the diene reactant is selected from the group consisting of 1,3-butadiene, isoprene, 2,3-dimethyl-1,3-butadiene, piperylene, 1-acetoxybutadiene, 1-acetoxy-2-methyl-1,3-butadiene and 1-acetoxy-3-methyl-1,3-butadiene.

9. A process as claimed in claim 8, wherein the carboxylic acid is selected from the group consisting of formic acid, acetic acid and propionic acid.

* * * * *